United States Patent [19]

Carlsson

[11] Patent Number: 5,895,920
[45] Date of Patent: Apr. 20, 1999

[54] DEVICE FOR DETECTING LIGHT FLUORESCENCE

[76] Inventor: Leon Carlsson, Lievagen 16, S-183 38, Täby, Sweden

[21] Appl. No.: 08/836,365

[22] PCT Filed: Nov. 14, 1995

[86] PCT No.: PCT/SE95/01349

§ 371 Date: Jul. 22, 1997

§ 102(e) Date: Jul. 22, 1997

[87] PCT Pub. No.: WO96/15438

PCT Pub. Date: May 23, 1996

[30] Foreign Application Priority Data

Nov. 14, 1994 [SE] Sweden ................... 9403908

[51] Int. Cl.[6] ................... G01N 21/03; G01N 21/64
[52] U.S. Cl. ................... 250/461.1; 356/318; 250/373
[58] Field of Search ................... 250/373, 458.1, 250/459.1, 461.1; 356/317, 318, 417

[56] References Cited

U.S. PATENT DOCUMENTS

| | | |
|---|---|---|
| 5,018,866 | 5/1991 | Osten ................... 356/318 |
| 5,484,571 | 1/1996 | Pentoney, Jr. et al. ................... 422/82.08 |

Primary Examiner—Constantine Hannaher
Assistant Examiner—Darren M. Jiron
Attorney, Agent, or Firm—John Lezdey & Assoc

[57] ABSTRACT

A device for detecting fluorescence generated in a sample medium in a cuvette tube irradiated with light for analysis purposes. The device includes a main element comprising a light source, an optical element mounted on the cuvette tube in optical contact therewith, and a photodetector. The light source is placed on the outside of the cuvette tube so as to send light into the tube in a direction essentially transversely to the longitudinal axis of the tube. The refractive index of the optical element is essentially the same as the refractive index of the wall of the cuvette tube. The photodetector functions to detect fluorescence light which falls on the detector after having passed in the cuvette tube via the optical element.

13 Claims, 6 Drawing Sheets

DEVICE FOR DETECTING LIGHT FLUORESCENCE

FIELD OF THE INVENTION

The present invention relates to a device for detecting fluorescence in a light-illuminated sample medium in a cuvette tube in the analysis of the sample medium, wherein the device includes a light source placed on the outside of the cuvette tube and functioning to transmit light into the tube essentially at right angles to its longitudinal axis, and an optical element which is mounted on said tube and spaced from the light source in the longitudinal direction of said tube.

BACKGROUND OF THE INVENTION

The detection of sample fractions is an important part of chemical analyses based on HPLC analysis (HPLC=High Performance Liquid Chromatography) and CE analysis (CE=Capillary Electrophoresis). Two procedures employed to this end are UV-absorption detection and fluorescence detection. It is known to use in the case of UV-absorption detection a light source which emits both UV light and visible light. In the case of fluorescence detection, the sample is irradiated with exciting light, therewith causing the sample molecules to fluoresce in a known manner. It is desirable to be able to perform the detection process in a measuring cell consisting of a narrow tube (capillary), both with regard to measuring absorption and fluorescence. In many cases, it is desired to effect the measuring process on-line, i.e. directly in the capillary tube, which forms a separation column for fractions of the sample medium flowing therethrough.

It is also known to perform UV-absorption detection by transmitting a light beam of appropriate wavelength through the cuvette tube, transversely to its longitudinal axis, and onto a photodetector placed on the opposite side of the tube, where the light intensity is detected. A decrease in light intensity between light source and photodetector will therewith constitute a measurement of the concentration of absorbent substances in the sample medium contained in the cuvette tube.

Different methods of increasing the optical path in absorbency measuring processes are also known to the art; Swedish Patent Specification No. 8100194-3 can be mentioned as an example in this respect. This publication discloses an arrangement in which mutually parallel light beams are emitted from a light source located at one end of a cuvette tube, and led into said tube through the medium of an optical element. Subsequent to its passage through the sample medium in the tube, the light is led out of the tube and light beams, which are parallel with the cuvette tube, are led into a detection device. The arrangement can also be used for fluorescence-detecting purposes.

SUMMARY OF THE INVENTION

The main object of the present invention is to provide a novel fluorescence detecting device of particularly simple construction and therewith relatively cheap to produce. The novel device shall also enable detection to be achieved with a high degree of sensitivity and with the least possible disturbance of the analysis.

These objects are achieved by virtue of the optical element enabling light to be reflected against a rotational-elliptical or rotational-parabolic surface of said element, wherein at least a part of said element is in optical contact with the wall of the cuvette tube and has a refractive index which exceeds the refractive index of the sample medium, and wherein a photodetector is arranged to detect fluorescence light which, after passage in the cuvette tube, falls on said tube through the medium of the optical element. The light source is preferably placed on the outside of a straight part of the cuvette tube, and the optical element is a light-collecting element, for instance in the form of a tube-mounted sleeve made, for instance, of quartz or plexiglass and constructed to focus onto the photodetector fluorescence light that passes through the tube.

A fluorescence-light detecting device of this kind is particularly well suited for use in combination with a known UV-absorption detecting device, wherein certain parts of this latter device may also be used for the fluorescence-light detecting device.

Advantageous embodiments of the novel fluorescence-light detecting device that have not been included in the aforegoing will be apparent from the following dependent Claims.

The novel fluorescence-light detecting device affords several advantages, such as:

Fluorescence light can be taken out at a place where the level of interfering light of excitation wavelength is very low.

Access for detection purposes is much improved at a distance from the excitation beam than in the proximity thereof.

It is relatively easy to obtain a combined UV-absorption and fluorescence-detecting device where the light intended for UV-absorption detection purposes can also be used at the same time to excite the sample medium for fluorescence measuring purposes. The ability to detect emitted fluorescence light in a simple manner without disturbing the absorption measuring process at a readily accessible location has decisive significance in the present context.

The invention will now be described in more detail with reference to preferred embodiments thereof and also with reference to the accompanying drawings.

DESCRIPTION OF THE PREFERRED EMBODIMENTS

Figure 1A:
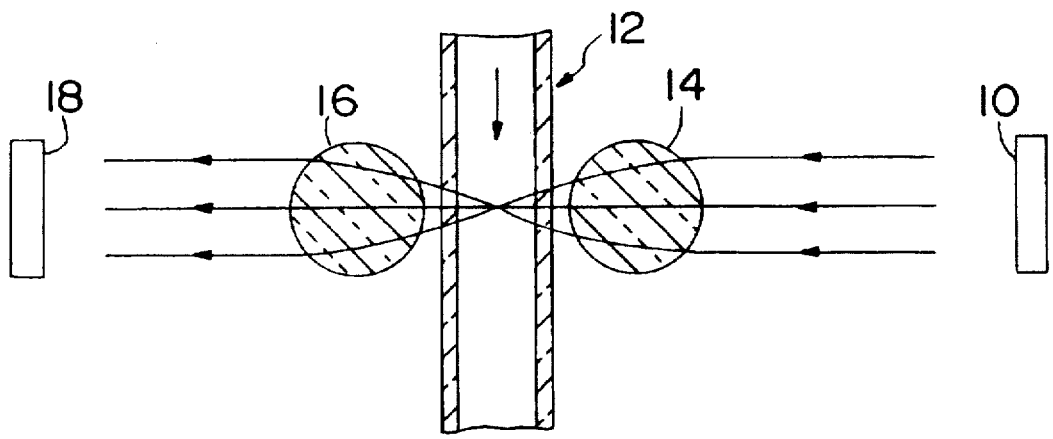
FIGS. 1a and 1b illustrate the beam path from a light source to a light detector in the case of an absorption measuring process, said Figures being respectively a sectional view in the longitudinal direction of the cuvette tube and a sectional view in the transverse direction of the tube.
Figure 1B:
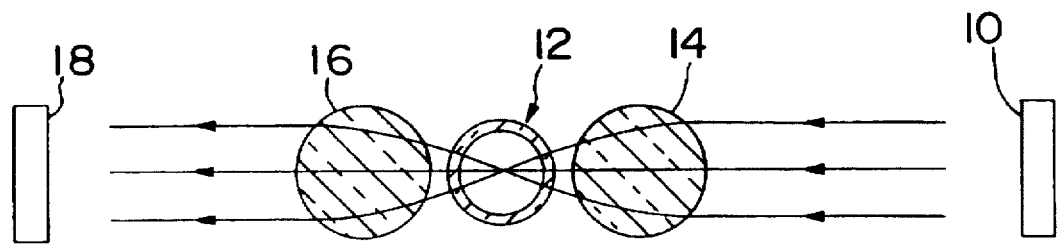

The arrangement illustrated in FIGS. 1a and 1b refers to the beam path in on-line UV-absorption measuring processes, wherein beams of light are directed from a light source 10 perpendicularly to a cuvette tube 12 in which sample medium to be analyzed flows. The beams of light are focused onto the centre of the cuvette tube 12 with the aid of a small, strongly light-refractive lens 14. In the illustrated embodiment, the lens is ball-shaped and may be made of quartz, for instance. The light beams exit on the opposite side of the cuvette tube 12 after having passed through the sample medium in said tube, and a further ball-shaped lens 16 is used to re-combine the light beams for measuring light intensity in a detector 18. The cuvette tube 12 of the illustrated embodiment may be made of quartz and may have an outer diameter in the order of 0.4 mm and an inner diameter in the order of 0.1–0.3 mm.

Figure 2:
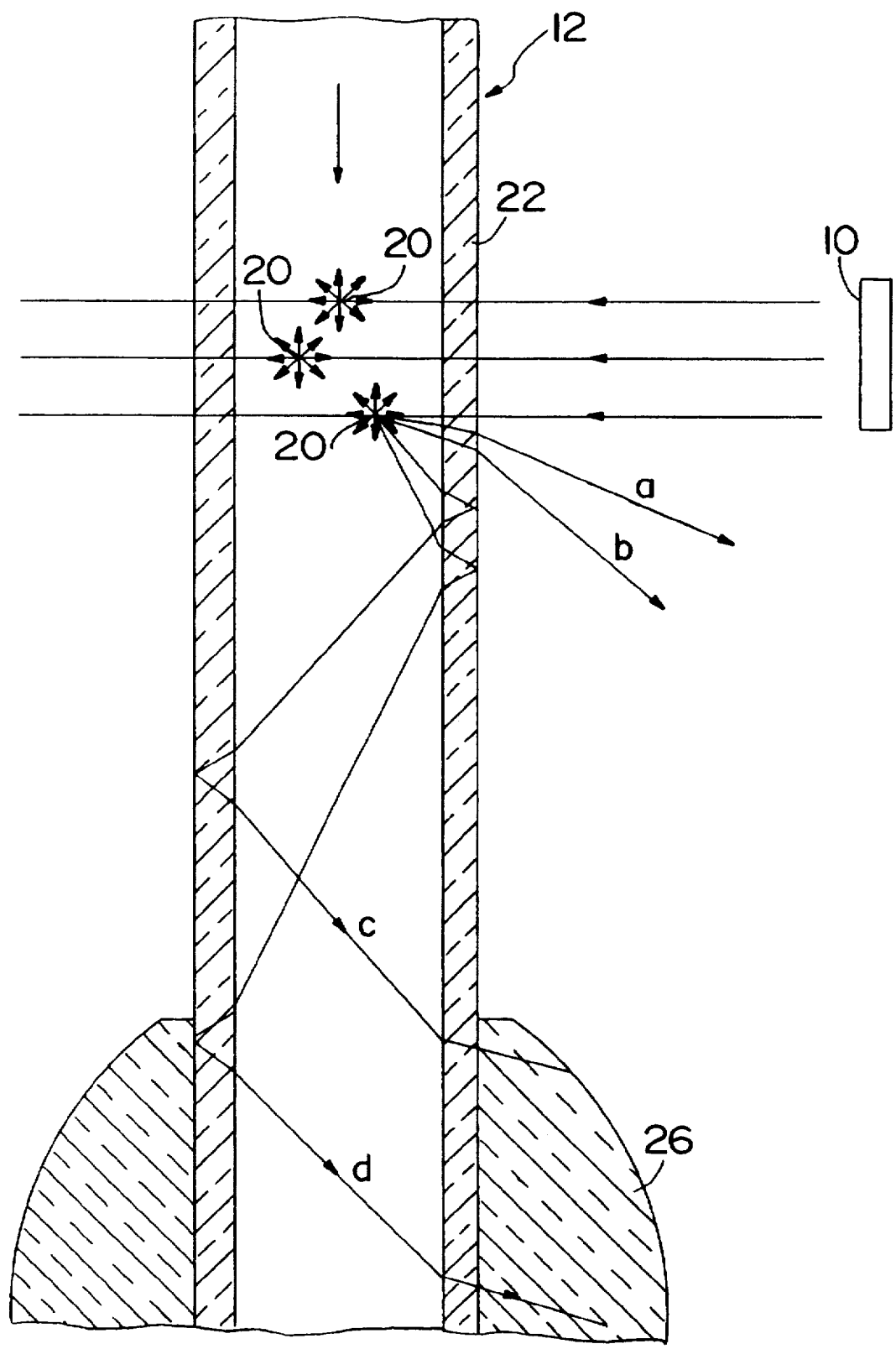
FIG. 2 is a sectional view in the longitudinal direction of the cuvette tube, and shows the beam path of light emitted from a light source, said light passing both transversely through the tube and along the same.

FIG. 2 also shows how fluorescence light can be obtained by irradiating the sample medium passing in the arrowed direction in the cuvette tube 12 with light of appropriate wavelength. In this regard, sample-substance molecules 20 present in the sample medium may be able to auto-fluoresce or may have been labelled with a fluorescent substance. The quantity of fluorescence emitted is a measurement of the quantity of sample substance that passes a measuring point. In the case of the FIG. 2 embodiment, the sample medium is irradiated with excitation light from the light source 10 which is located on the outside of a straight part of the cuvette and the light beams pass through the wall 22 of the cuvette tube in the same way as that shown in FIGS. 1a and 1b. In this case, fluorescence light is emitted by the molecules 20 in the sample medium in all directions. It is now a matter of capturing this fluorescence light in a suitable manner. Part of the light passes out through the cuvette wall 22 and can be captured by an objective (not shown), e.g. the light beams a and b. However, such a method has the drawback that the objective captures at the same time parts of the intensive excitation light which as a result of reflections generates a light corona around the cuvette tube 12. This results in a very high level of stray light which, naturally, reduces detection sensitivity.

If a liquid immersion medium or a solid plastic material under pressure, as mentioned before, is utilized to give optic contact the cuvette tube 12 can be exchanged by the user. If, on the other side, fusion, gluing or molding together is used to give optic contact the optical element 26 will be fixed to the cuvette tube. In order to simplify the exchange of the cuvette tube 12 it is then also possible, according to the invention, to combine the cuvette tube 12, the optical element 26 and the mirror element 34, 36, if any, to a separate replaceable cassette which can easily be placed in the device which can, for the rest, be unchanged.

Another method of measuring the emitted fluorescence light involves capturing a part of the light that does not exit through the cuvette wall 22. When the direction of the emitted light deviates by less than a certain angle from the longitudinal axis of the cuvette tube 12, the light will be reflected totally at the interface between the cuvette wall 22 and the air surrounding the cuvette tube 12. For instance, this angle will be approximately 41" when the medium contained by the cuvette tube 12 is water. That part of the fluorescence light which is prevented in this way from exiting from the cuvette tube 12 propagates from the excitation location in both directions, in the same way as in a light guide; see for instance the light beams c and d.

Figure 3A:
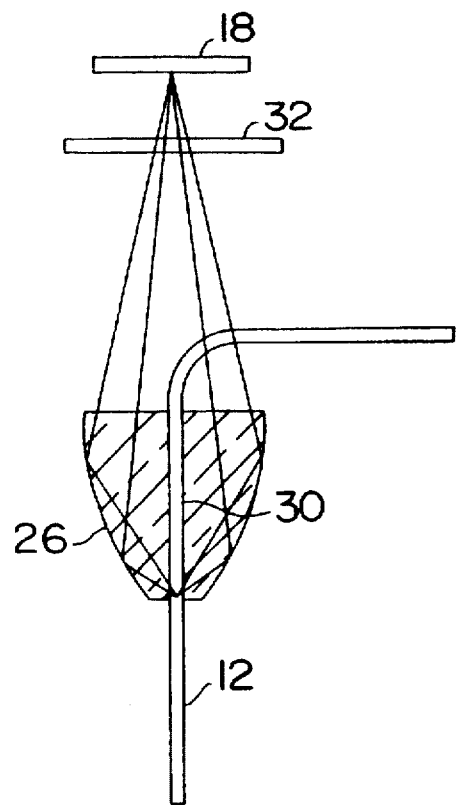
FIGS. 3a–3c are cross-sectional views taken in the longitudinal direction of the cuvette tube and showing three different embodiments of elements in the novel fluorescence-detecting device.
Figure 3B:
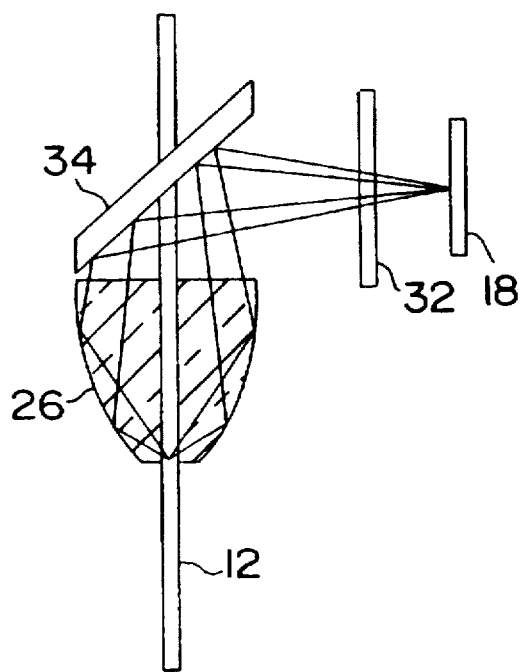
Figure 3C:
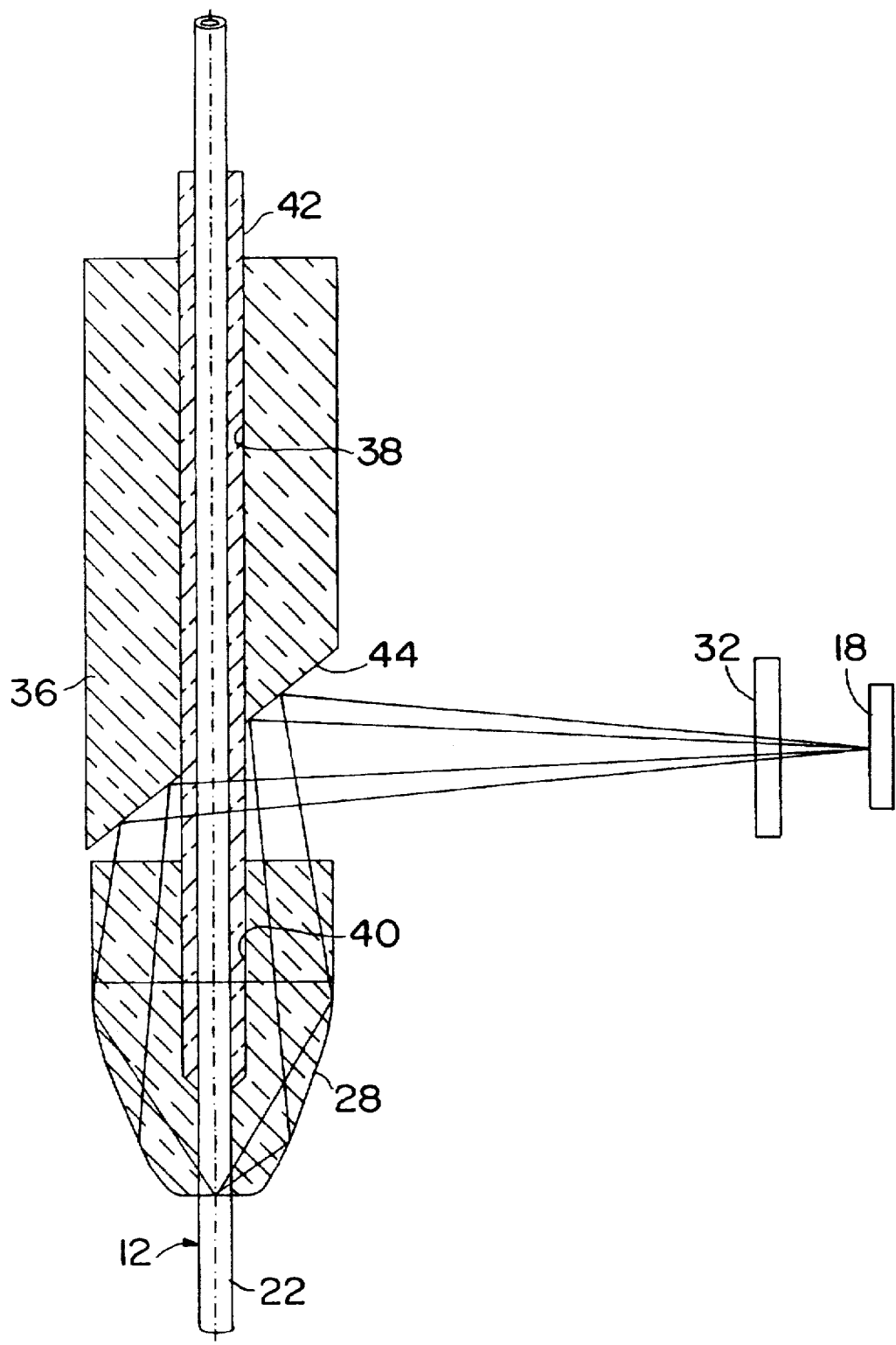

As will be seen from FIGS. 3a–3c in particular, the present invention provides a device which is particularly suited for leading-out the fluorescence light enclosed in the cuvette tube 12 at a point suitably distanced from the excitation location and thus for making the fluorescence light available for measurement with the aid of a photodetector 18. The fluorescence light is guided to its place of exit with the aid of an optical element 26 or 28, the refractive index of which must be higher than the refractive index of the sample medium enclosed in the tube 12 and which is generally made of a material that has essentially the same refractive index as the wall 22 of the cuvette tube.

The actual principle in which fluorescence light is guided out of the cuvette tube 12 is shown particularly in the bottom part of FIG. 2. In this case, optical contact between the tube wall 22 and the optical element 26 has been achieved by fusion melting, gluing, casting or with the aid of a liquid immersion medium. However, it is also possible to use plastic material in a solid state capable of providing optical contact between the tube wall 22 and the optical element 26 under pressure.

An embodiment of the optical element 26 and detection of fluorescence light emitting therefrom is illustrated in FIG. 3a. In this case, the light-collecting optical element 26 is in the form of a sleeve having a central through-penetrating hole 30. The cuvette tube 12 is inserted through the hole 30 and affixed to the optical element 26 in one of the ways mentioned above. The optical element has essentially the shape of a truncated, solid rotational-ellipsoid. In this way, all of the fluorescence light beams passing into the optical element 26 will be focused onto a common point along the axis line of the tube 12, where the photodetector 18 is located, as a result of internal total reflection in the mantle surface of the optical element. A barrier filter 32 is placed between the optical element 24 and the photodetector 18 in order to eliminate light of undesirable wavelengths.

FIG. 3b illustrates a particularly advantageous embodiment of the invention. The optical element 26 of the FIG. 3b illustration has the same design as in the FIG. 3a embodiment and thus strives to focus fluorescence light onto a point on the axis line of the cuvette tube 12. In this case, however, there is placed in front of the focusing point a mirror element 35 by means of which the beams of fluorescence light are caused to radiate together towards a point that is located outside a straight part of the cuvette tube 12. Similar to the case of the FIG. 3a embodiment, a photodetector 18 is placed in the focusing point and a barrier filter 32 is placed in front of said point.

FIG. 3c illustrates an embodiment in which the optical element 28 and the mirror element 36 are combined to form a single unit. These elements may be comprised of the same material, for instance quartz or plexiglass, and are aligned linearly in relation to one another and provided with through-penetrating holes 38, 40. A centering tube 42 is inserted into said holes 38, 40 so as to extend completely through the mirror element 36 and also in through the major part of the optical element 28. The arrangement is such that the two elements 28, 36 will fit tightly on the tube 42 and be fixed relative thereto. At the narrower end of the optical element 28, through which end the tube 42 does not extend, the hole 40 provided in said element has a smaller diameter than the hole in the part into which the tube 42 is inserted. The tube 42 fits tightly on the cuvette tube 12 and is fixed relative thereto. The material from which the tube 42 is made is not critical, although the tube may conveniently be made of stainless steel.

The reflective surface 44 of the mirror element 36 defines an angle of 45° with the axis line of the cuvette tube 12. The beams of fluorescence light that are reflected by the reflective surface 44 will therefore radiate together towards the detector 18 in a point which is located on a line that extends at right angles to the point of intersection between the axis line of the cuvette tube 12 and the centre of the reflective surface 44.

Figure 4A:
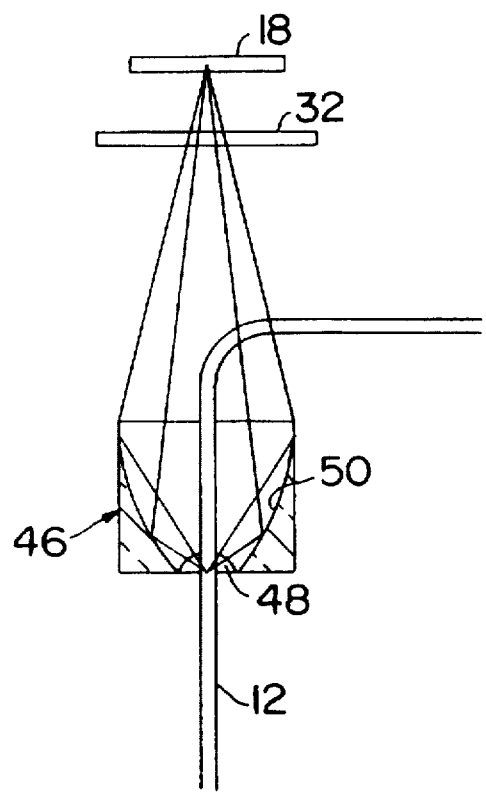
FIGS. 4a and 4b are cross-sectional views taken in the longitudinal direction of the cuvette tube and showing two further advantageous embodiments of elements included in the novel detecting device.
Figure 4B:
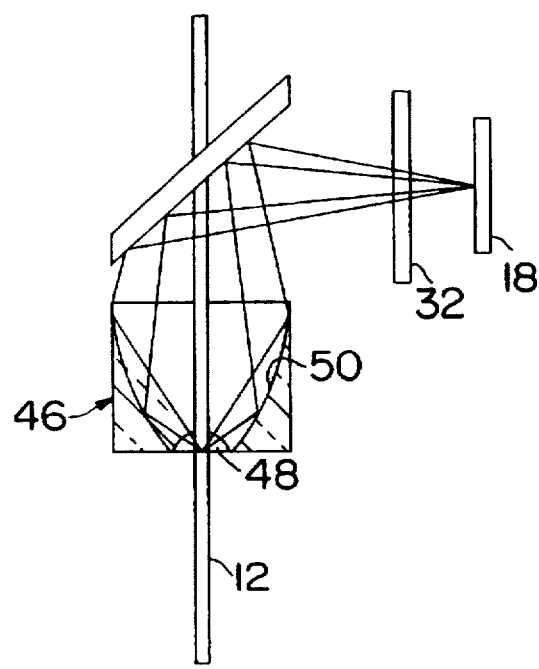

Instead of using a solid ellipsoidal body as an optical element in accordance with the embodiments illustrated in FIGS. 3a and 3b, the embodiments illustrated in FIGS. 4a and 4b include an optical element 46 of another design. The optical element 46 of the embodiments illustrated in FIGS. 4a and 4b is comprised of two components, vis an essentially hemispherical solid body 48 which although being in optical contact with the cuvette 12 has no focusing effect, and an internally reflective rotational-ellipsoidal shell 50 which functions to focus the light beams. The outwardly curving surface of the hemispherical solid body 48 protrudes into the shell 50 at the narrower end thereof, as illustrated in the Figure, and the refractive index of the hemispherical solid body 48 is the same as the reflective index of the solid optical elements 26 of the FIGS. 3a and 3b embodiments.

Figure 5:
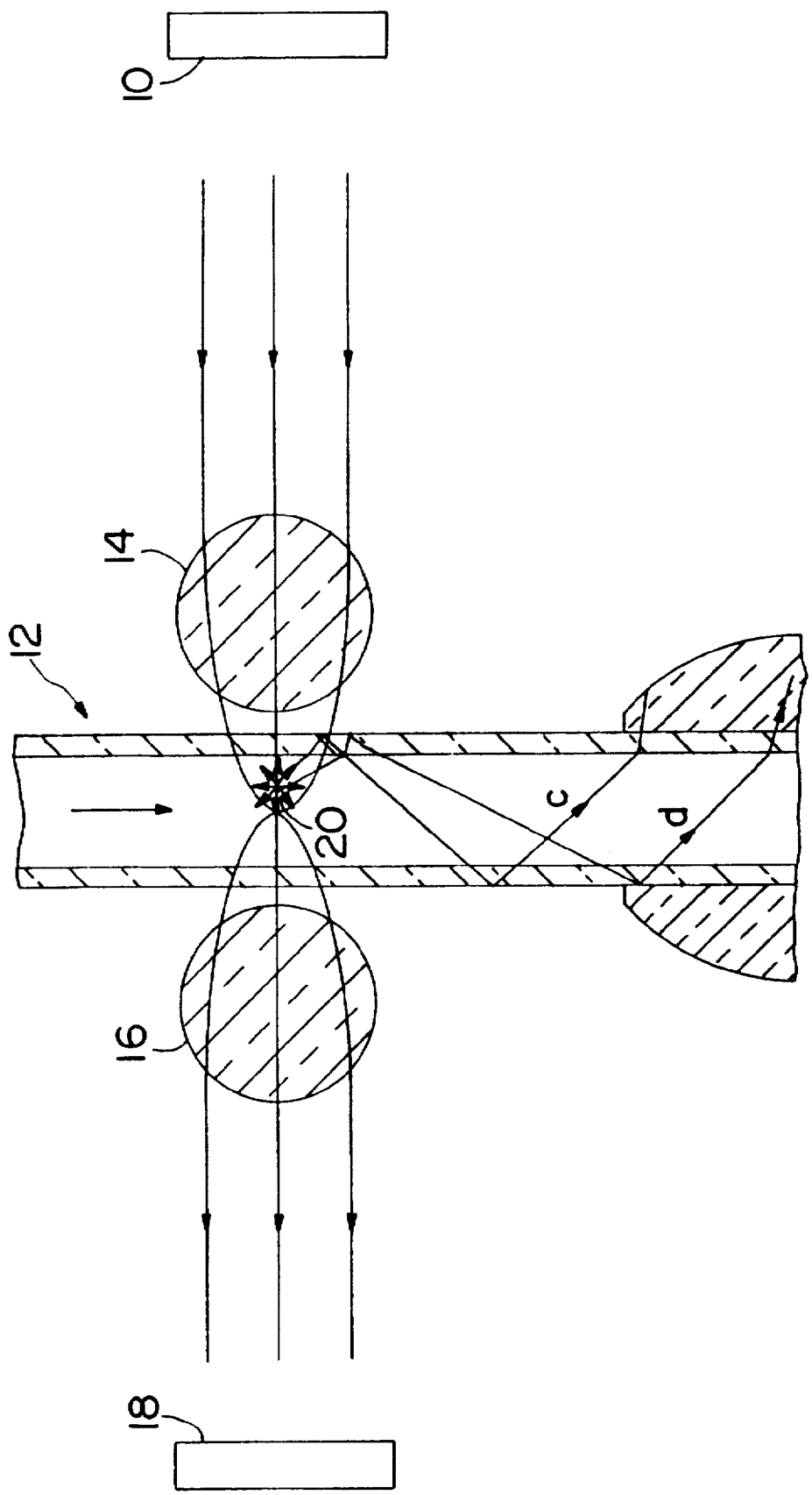
FIG. 5 is a sectional view in the longitudinal direction of the cuvette tube in another embodiment.

FIG. 5 illustrates an embodiment in which fluorescence and UV absorption are detected in combination. Essentially, FIG. 5 is a combination of FIG. 1a and FIG. 2.

It will be understood that the aforedescribed detecting device can be modified in several ways within the scope of the inventive concept. For instance, the fluorescence light may be led directly from the optical element to a detector placed on one side of the cuvette tube, with the aid of fibreoptics. The optical element may also have a form different to that described with reference to the illustrated embodiments. For instance, the element may have the form of a frusto-conical rotational-paraboloid, and a lens may be provided for focusing light beams exiting from the paraboloid onto the photodetector.

I claim:

1. A device for detecting fluorescence generated by irradiating with light a sample medium contained in a cuvette tube for analysis purposes, wherein the device includes a light source which is placed on the outside of the cuvette tube so as to transmit light into said tube in a direction essentially at right angles to the longitudinal axis of the tube, and an optical element which is placed on the tube at a location which is distanced from the light source as seen in the longitudinal direction of the tube, said optical element enabling light to be reflected on rotational-elliptical or rotational-parabolic surfaces thereof, wherein at least a part of said element is in optical contact with a wall of the cuvette tube and has a refractive index which is higher than the refractive index of the sample medium, and a photodetector arranged to detect fluorescence light which falls thereon after passage in the cuvette tube, via the optical element.

2. The device according to claim 1, wherein the light source is placed on the outside of a straight part of the cuvette tube; and said optical element is a light-collecting element in the form of a sleeve mounted on the cuvette tube and made of quartz or plexiglass; and in the light-collecting element functions to focus onto the photodetector fluorescence light that passing in the cuvette tube.

3. The device according to claim 1 wherein said optical element has essentially the form of a truncated solid rotational-ellipsoid.

4. The device according to claim 1 wherein the optical element is essentially in the form of a truncated, solid rotational-paraboloid, characterized by a lens which functions to focus light beams exiting from the rotational-paraboloid onto the photodetector.

5. The device according to claim 1, wherein said optical element is comprised of an essentially hemispherical solid body which is in optical contact with the cuvette tube and a light-focusing, internally reflective rotational-ellipsoidal shell wherein the outwardly curved surface of the solid body protrudes into the shell at its narrower end.

6. The device according to claim 1 wherein said photodetector is placed on the outside of a straight part of the cuvette tube.

7. The device according to claim 6, which includes a mirror element having a mirror surface placed between the optical element and the photodetector so as to direct the fluorescence light onto the photodetector placed on one side of the cuvette tube.

8. The device according to claim 7, wherein said mirror element is an integral part of the optical element.

9. The device according to claim 8, wherein the integral unit consisting of said mirror element and said optical element includes a central hole into which a tube enclosing the cuvette tube is at least partially inserted.

10. The device according to claim 1 wherein a barrier filter placed between said optical element and said photodetector so as to eliminate light of undesirable wavelengths, and wherein said device includes said mirror element, the barrier filter is placed downstream of said mirror element as seen in the beam direction.

11. The device according to claim 1 wherein a plastic material in a solid state is arranged to provide optical contact between the tube wall and the optical element under pressure.

12. The device according to claim 1 in combination with a UV-absorption detection device, wherein the UV-detection device includes a light source which is placed on the outside of the cuvette tube so as to send light into said tube in a direction generally transversely to the longitudinal axis of said tube, and a photodetector placed on the diametrically opposite side of the cuvette tube for detecting UV light that has passed through the sample medium in said cuvette tube, characterized by using the same light source for both fluorescence and UV-absorption detection.

13. The combined device according to claim 12, which includes a replaceable cassette containing a cuvette tube, optical element and mirror element.

* * * * *